(12) United States Patent
Badoer et al.

(10) Patent No.: US 9,371,515 B2
(45) Date of Patent: Jun. 21, 2016

(54) MESENCHYMAL STEM CELLS AND BONE-FORMING CELLS

(75) Inventors: Cindy Badoer, Ittre (BE); Enrico Bastianelli, Rhode-Saint-Genese (BE); Xavier Pesesse, Bierghes (BE)

(73) Assignee: Bone Therapeutics S.A., Gosselies (BE)

( * ) Notice: Subject to any disclaimer, the term of this patent is extended or adjusted under 35 U.S.C. 154(b) by 282 days.

(21) Appl. No.: 12/991,120

(22) PCT Filed: May 7, 2009

(86) PCT No.: PCT/EP2009/055549
§ 371 (c)(1),
(2), (4) Date: Nov. 30, 2010

(87) PCT Pub. No.: WO2009/135905
PCT Pub. Date: Nov. 12, 2009

(65) Prior Publication Data
US 2011/0262404 A1 Oct. 27, 2011

(30) Foreign Application Priority Data
May 7, 2008 (EP) .................................. 08155764

(51) Int. Cl.
| | | |
|---|---|---|
| A61P 19/08 | (2006.01) |
| C12N 5/0775 | (2010.01) |
| C12N 5/077 | (2010.01) |
| A61K 35/12 | (2015.01) |
| A61K 35/28 | (2015.01) |

(52) U.S. Cl.
CPC .............. *C12N 5/0675* (2013.01); *A61K 35/28* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *A61K 2035/124* (2013.01); *C12N 2501/113* (2013.01); *C12N 2501/115* (2013.01); *C12N 2501/119* (2013.01); *C12N 2501/22* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 5,736,396 A | 4/1998 | Bruder et al. | |
| 5,811,094 A | 9/1998 | Caplan et al. | |
| 5,827,740 A | 10/1998 | Pittenger | |
| 5,837,539 A | 11/1998 | Caplan et al. | |
| 5,972,703 A | 10/1999 | Long et al. | |
| 7,470,538 B2 | 12/2008 | Laughlin et al. | |
| 2005/0019910 A1* | 1/2005 | Takagi et al. | 435/370 |
| 2006/0051330 A1* | 3/2006 | Hossfeld et al. | 424/93.21 |
| 2006/0134781 A1* | 6/2006 | Yang et al. | 435/366 |
| 2006/0205071 A1* | 9/2006 | Hasson et al. | 435/366 |
| 2007/0082394 A1* | 4/2007 | Moscatello | 435/325 |
| 2008/0306004 A1* | 12/2008 | Tang | 514/12 |

FOREIGN PATENT DOCUMENTS

| | | |
|---|---|---|
| JP | 2005-287479 | 10/2005 |
| JP | 2006-230316 | 9/2006 |
| JP | 2008-022822 | 2/2008 |
| WO | WO 94/22463 A | 10/1994 |
| WO | 00/07639 | 2/2000 |
| WO | 0134775 A1 | 5/2001 |
| WO | 2006134951 A1 | 12/2006 |
| WO | 2007/093431 | 8/2007 |
| WO | WO 2007/093431 A | 8/2007 |
| WO | WO 2007085210 A2 * | 8/2007 |
| WO | 2008018190 A1 | 2/2008 |

OTHER PUBLICATIONS

Olmsted-David, Elizabeth A; et al; "Primitive adult hematopoietic stem cells can function as osteoblast precursors" Proceedings of the National Academy of Science, 100, 15877-15882, 2003.*
Sotiropoulou, Panagiota A; et al; "Characterization of the Optimal Culture Conditions for Clinical Scale Production of Human Mesenchymal Stem Cells" Stem Cells, 24, 462-471, 2006.*
Lee, C. Chang I.; et al; "Comparison of Growth and Differentiation of Fetal and Adult Rhesus Monkey Mesenchymal Stem Cells" Stem Cells and Development, 15, 209-220, 2006.*
Brugger, W; et al; "Ex vivo expansion of enriched peripheral blood CD34+ progenitor cells by stem cell factor, interleukin-1 beta (IL-1 beta), IL-6, IL-3, interferon-gamma, and erythropoietin" Blood, 81, 2579-2584, 1993.*
Airas et al., "Lymphocyte-Vascular Adhesion Protein-2 Is a Novel 70-kDa Molecule Involved in Lymphocyte Adhesion to Vascular Endotehlium," 1993, J Immunol 151: 4228.
Alhadlaq et al., "Mesenchymal Stem Cells: Isolation and Therapeutics," 2004, Stem Cells Dev 13: 436-48.
Barberi et al., "Derivation of Multipotent Mesenchymal Precursors from Human Enbryonic Stem Cells," 2005, PLoS Med 2: e161.
Bellon et al., "Identification and expression of two forms of the human transforming growth factor-β-binding protein endoglin with distinct cytoplasmic region," 1993, Eur J Immunol 23: 2340.
Civin et al., "Antigenic Analysis of Hematopoiesis. III. A Hemotopoietic Progenitor Cell Surface Antigen Defined by a Monoclonal Antibody Raised against KG-1a Cells," 1984, J Immunol 133: 157.

(Continued)

*Primary Examiner* — Renee Claytor
*Assistant Examiner* — David Berke-Schlessel
(74) *Attorney, Agent, or Firm* — McDonnell Boehnen Hulbert & Berghoff LLP

(57) ABSTRACT

The invention relates to a new type of mesenchymal stem cells (MSC) which co-express at least one mesenchymal marker, preferably at least CD105 and CD34. Also provided are bone-forming cells having an analogous phenotype. The invention also provides the cells and cell populations, as well as further products comprising such and uses thereof in bone therapy.

8 Claims, 7 Drawing Sheets

(56) References Cited

OTHER PUBLICATIONS

Connolly et al., "Injectable Bone Marrow Preparations to Stimulate Osteogenic Repair," 1995, Olin Orthop 313: 8-18.
Cook et al., "Characterization and development of RGD-peptide-modified poly(lactic acid-co-lysine) as an interactive, restorable biomaterial," 1997 J. Biomed. Mater. Res. 35:513-523.
Craig et al., "Expression of Thy-1 on Human Hematopoietic Progenitor Cells," 1993, J Exp Med 177: 1331.
Dainiak et al., "Methods in Cell Separations," 2007, Adv Biochem Eng Biotechnol 106: 1-18.
D'Ippolito et al., "Age-related osteogenic potential of mesenchymal stromal stem cells from human vertebral bone marrow," 1999, J Bone Miner Res. 14: 1115-22.
Eghbali-Fatourechi et al., "Characterization of circulating osteoblast lineage cells in humans," 2007, Bone 40: 1370-7.
Fernley et al., "Kinetic Behaviour of Calf-Intestinal Alkaline Phosphatase with 4-Methylumbelliferyl Phosphate," 1965, Biochem J. 97: 95-103.
Gangji et al., "Stem cell therapy for osteonecrosis of the femoral head," 2005, Expert Opin Biol Ther 5: 437-42.
Gene accession No. P28906 (seq.5 version 2, entry version 74).
Gene accession No. P17813 (seq. version 2, entry version 91).
Gene accession No. P21589 (seq. version 1, entry version 87).
Gene accession No. PO4216 (seq. version 2, entry version 94).
Gregory et al., "An Alizarin red-based assay of mineralization by adherent cells in culture: comparison with cetylpyridinium chloride extraction," 2004, Analytical Biochemistry 329: 77-84.
Jaiswal et al., "Osteogenic Differentiation of Purified Culture-Expanded Human Mesenchymal Stem Cells in Vitro," 1997, J Cell Biochem 64: 295-312.
Letarte et al. 1995, In: Leukocyte Typing V, ed. SF Schlossman et al., Oxford University Press, Oxford, p. 1756-1759.
Mikos et al., "Laminated three-dimensional biodegradable foams for use in tissue engineering," 1993, Biomaterials 14: 323.
Mikos et al., "Preparation and characterization of poly(L-lactic) foams," 1994, Polymer 35:1068.
Pittenger et al., "Multilineage Potential of Adult Human Mesenchymal Stem Cells," 1999, Science 284: 143-7.
Prockop, "Marrow Stromal Cells as Stem Cells for Nonhematopoietic Tissues," 1997, Science 276: 71-4.
Simmons et al., "Molecular Cloning of a cDNA Encoding CD34, A Sialomucin of Human Hematopoietic Stem Cells," 1992, J Immunol 148: 267-271.
Skjodt et al., "Vitamin D metabolites regulate osteocalcin synthesis and proliferation of human bone cells in vitro," 1985, J Endocrinol 105: 391-6.
Thomson et al., "Production and characterization of monoclonal antibodies to the glycosyl phosphatidylinositol-anchored lymphocyte differentiation antigen ecto-5'-nucleotidase (CD73)," 1990, Tissue Antigens 35: 9.
Weiss et al., "Isolation and characterizations of a cDNA encoding a human liver/bone/kidney-type alkaline phosphatase," 1986, PNAS 83: 7182-7186.
Young et al., "Human Reserve Pluripotent Mesenchymal Stem Cells Are Present in the Connective Tissues of Skeletal Muscle and Dermis Derived From Fetal, Adult, and Geriatric Donors," 2001, Anat Rec 264: 51-62.
Zuk et al., "Multilineage Cells from Human Adipose Tissue: Implications for Cell-Based Therapies," 2001, Tissue Eng 7: 211-28.
Yoshimura Kotaro et al.: "Characterization of freshly isolated and cultured cells derived from the fatty and fluid portions of liposuction aspirates," Journal of Cellular Physiology, vol. 208, No. 1, Jul. 2006, pp. 64-76.
Mitchell J.B. et al.: "Immunophenotype of Human Adipose-Derived Cells: Temporal Changes in Stromal-Associated and Stem Cell-Associated Markers," Stem Cells, Alphamed Press, Dayton, OH, US, vol. 24, No. 2, Feb. 1. 2006, pp. 376-385.
Oedayrajsingh-Varma M. J. et al.: Adipose tissue-derived mesenchymal stem cell yield and growth characteristics are affected by the tissue-harvesting procedure, Cytotherapy, ISIS Medical Media, Oxford, vol. 8, No. 2, May 1, 2006, pp. 166-177.

Bos Van Den C. et al.: "Human Mesenchymal Stem Cells Respond to Fibroblast Growth Factors," Human Cell—Hito Saibo Kenkyukai Zasshi, Tokyo, JP, vol. 10, No. 1, Mar. 1, 1997, pp. 45-50.
Dan Y Y et al.: "Isolation of multipotent progenitor cells from human fetal liver capable of differentiating into liver and mesenchymal lineages," Proceedings of the National Acadmey of Sciences of the United States of America, vol. 103, No. 26, Jun. 2006, pp. 9912-9917.
Majumdar M. K. et al.: Human marrow-derived mesenchymal stem cells (MSCs) express hematopoietic cytokines and support long-term hematopoiesis when differentiate toward stromal and osteogenic lineages, Journal of Hematotherapy and Stem Cell Research, Mary Ann Liebert, New York, NY, US, vol. 9, No. 6, Dec. 1, 2000, pp. 841-848.
Pittenger M.F. et al.: "Mulitlineage potential of adult human mesenchymal stem cells," Science, American Association for the Advancement of Science, US Washington, DC, vol. 284, No. 5411, Apr. 2, 1999, pp. 143-147.
Gangji et al.: "Treatment of osteonercrosis of the femoral head with implantation of preosteoblastic cells into the necrotic zone: Case report," Bone, Pergamon Press, Oxford, GB, vol. 40, No. 6, Jun. 1, 2007, p. S47.
Hattori H. et al.: "Osteogenic Potential of Human Adipose Tissue-Derived Stromal Cells as an Alternative Stem Cell Source," Cells Tissues Organs, Karger, Basel, CH, vol. 178, No. 1, Jan. 1, 2004, pp. 2-12.
Ling Ling et al.: "Sulfated glycosaminoglycans mediate the effects of FGF2 on the osteogenic potential of rat calvarial osteoprogenitor cells," Journal of Cellular Physiology, Wiley Liss, New York, NY, US, vol. 209, No. 3, Dec. 1, 2006, pp. 811-825.
Sotiropoulou P. et al.: "Characterization of the Optimal Culture Conditions for Clinical Scale Production of Human Mesenchymal Stem Cells," Stem Cells Alphamed Press, Dayton, OH, US, vol. 24, No. 2, Feb. 1, 2006, pp. 462-471.
Kilroy Gail E. et al.: "Cytokine profile of human adipose-derived stem cells: Expression of angiogenic, hematopoietic and pro-inflammatory factors," Journal of Cellular Physiology, Wiley Liss, New York, NY, US, vol. 212, No. 3, Sep. 1, 2007, pp. 702-709.
Chamberlain, Giselle et al.: "Concise Review: Mesenchymal Stem Cells: Their Phenotype, Differentiation Capacity, Immunological Features, and Potential for Homing," Stem Cells (2007), vol. 25, pp. 2739-2749.
Dominici, M. et al.: "Minimal criteria for defining multipotent mesenchymal stromal cells. The International Society for Cellular Therapy position statement," Cytotherapy (2006), vol. 8, Issue: 4, Publisher: Informa UK Ltd UK, pp. 315-317.
Daniele Noël, et al.: "Cell specific differences between human adipose-derived and mesenchymal-stromal cells despite similar differentiation potentials," Experimental Cell Research, (Apr. 15, 2008), vol. 314, Issue 7, pp. 1575-1584.
Quirici Net Al: "Differentiation and Expansion of Endothelial Cells From Human Bone Marrow CD133+ Cells", 2001, British Journal of Haematology, 115:186-194.
Eliopoulos, Nicoletta et al.,"Allogeneic marrow stromal cells are immune rejected by MHC class I-and class II-mismatched recipient mice," 2005, Blood, 106:4057-4065.
Pierellli, Luca et al., "CD34+/CD1 05+ cells are enriched in primitive circulating progenitors residing in the GO phase of the cell cycle and contain all bone marrow and cord blood CD34+/CD38 low/-precursors," British Journal of Haematology, 108:610-620.
Campagnoli et al., "Identification of mesenchymal stem/progenitor cells in human first-trimester fetal blood, liver, and bone marrow," 2001, Blood, 98:2396-2402.
O'Donoghue et al., "Fetal stem cells," 2004, Best Practice & Research Clinical Obstetrics and Gynaecology, 18:853-875.
Copland et al., "CD34 expression on murine marrow-derived mesenchymal stromal cells: impact on neovascularization," 2008, Exp. Hematol., 36:93-103.
Kaiser et al., "BM cells giving rise to MSC in culture have a heterogeneous CD34 and CD45 phenotype," 2007, Cytotherapy, 9:439-450.
Lin et al., "Is CD34 truly a negative marker for mesenchymal stromal cells?" 2012, Cytotherapy, 14:1159-1163.
Simmons et al., "CD34 Expression by Stromal Precursors in Normal Human Adult Bone Marrow," 1991, Blood 78:2848-2853.

* cited by examiner

A

B

MESENCHYMAL STEM CELLS AND BONE-FORMING CELLS

This application is a US national phase of International Application No. PCT/EP2009/055549 filed on May 7, 2009, which claims the benefit of European Patent Application No. EP 08155764.7 filed on May 7, 2008, the disclosures of which are incorporated herein by reference in their entirety.

FIELD OF THE INVENTION

The invention relates in general to the fields of cell phenotype and cell differentiation, and to uses of cells in medicine. More specifically, the invention identifies a new mesenchymal stem cell (MSC) type and a new bone-forming cell type, and concerns osteogenic differentiation of said MSC, and therapeutic and prophylactic applications of said MSC and said bone-forming cells in bone diseases.

BACKGROUND OF THE INVENTION

Transplantation of stem cells capable of or having a propensity for undergoing osteogenic differentiation is a promising avenue for the treatment of bone-related diseases, especially when the treatment requires production of new bone.

Bone marrow stromal cells or mesenchymal stem cells (abbreviated as BMSC or MSC) can be readily isolated and expanded from adult bone marrow and several other tissues, based on the adherence of these cells to tissue culture plastic. MSC mostly demonstrate a tri-potential, mesoderm-related fate, i.e., the capacity to undergo osteogenic, adipocytic and chondrocytic differentiation (Pittenger et al. 1999. Science 284: 143-7), although MSC capable of producing neural, liver and muscle cells have also been reported (Prockop 1997. Science 276: 71-4).

MSC may be defined by expression of soluble and surface markers, including among others CD105, CD90 and CD73. Moreover, the prior art generally shows MSC as negative for the CD34 antigen, which is instead known to be highly expressed in immature blood and endothelial cells. In particular, CD34-positive, bone marrow originated MSC have not been described previously. Also, enhanced osteogenic and osteoregenerative properties have not been described previously for CD34-positive MSC, and particularly for CD34-positive MSC originated from bone marrow.

Bone marrow transplantation has been employed to treat bone disorders (Gangji et al. 2005. Expert Opin Biol Ther 5: 437-42). However, MSC may only represent a minor proportion of all cells present in bone marrow samples, and can moreover display variable tendencies for osteogenic differentiation, such that a considerable proportion of so-transplanted cells would not eventually contribute to the formation of the desired bone tissue. Indeed, it has been shown that only about 14% of human adult mesenchymal stem cell progenitors maintained an osteogenic potential (D'Ippolito et al. 1999. J Bone Miner Res. 14: 1115-22).

In view thereof, there exists a continuing need to improve the yield of production of osteoprogenitors, osteoblasts or bone-forming cells from mesenchymal stem cells.

SUMMARY OF THE INVENTION

The present inventors have determined that a small subset of isolated and optionally expanded MSC cells co-express at least one mesenchymal marker, such as for example CD90 or CD105, more preferably at least CD105, with CD34, a marker that has been usually considered to represent immature blood and endothelial character of cells.

Compared to general MSC cell populations, this new cell type expresses significant levels of alkaline phosphatase (ALP), a bone-cell marker, and can synthesise and mineralise new bone matrix. Hence, the cells possess a relatively high potential to produce bone-forming cells useful for bone reconstruction. The inventors have also observed that the cells can be greatly expanded, whereby adequate quantities of bone-forming cells can be generated for cell-based therapies particularly for bone disorders. The present inventors succeeded to enrich MSC cells for the above cell subtype, which then maintains its phenotypic and biological properties.

An aspect of the invention provides an isolated mesenchymal stem cell (MSC) characterised in that it co-expresses at least one mesenchymal marker and CD34.

A further aspect provides a method for obtaining MSC cells co-expressing at least one mesenchymal marker and CD34 comprising enriching or isolating from a population of MSC cells a subset of cells which co-express said at least one mesenchymal marker and CD34. An embodiment provides a method for obtaining MSC cells co-expressing at least one mesenchymal marker and CD34 comprising (a) isolating MSC cells from a sample of a subject; (b) optionally enriching and/or expanding the MSC cells of (a); and (c) enriching or isolating from the MSC cells of (a) or (b) a subset of cells which co-express at least one mesenchymal marker and CD34.

Another aspect relates to MSC cells obtainable by a method comprising isolating from a population of MSC cells a subset of cells which co-express at least one mesenchymal marker and CD34. An embodiment provides MSC cells obtainable by steps comprising (a) isolating MSC cells from a sample of a subject; (b) optionally expanding the MSC cells of (a); and (c) isolating from the MSC cells of (a) or (b) a subset of cells which co-express at least one mesenchymal marker and CD34.

Also provided is a cell population comprising the isolated mesenchymal stem cells (MSC) co-expressing at least one mesenchymal marker and CD34 as defined in any of the preceding aspects.

It shall be appreciated that the present invention also encompasses various manipulations of MSC cells and cell populations as taught above, such as MSC cells co-expressing at least one mesenchymal marker and CD34 and cell populations comprising such MSC cells, including inter alia culturing, maintaining, expanding, enriching (e.g., by sorting) and post-enrichment expanding of said MSC cells and cell populations.

A further aspect provides a method for in vitro expanding of isolated mesenchymal stem cells (MSC), preferably isolated MSC which co-express at least one mesenchymal marker and CD34 as taught herein, comprising exposing said MSC cells to a haematopoietic growth factor and/or an angiogenic growth factor, preferably to a haematopoietic growth factor and an angiogenic growth factor, e.g., to one or more haematopoietic growth factors and/or one or more angiogenic growth factors.

This method may also be adapted for obtaining from an MSC population (i.e., a relatively more heterogeneous MSC population) MSC cells which co-express at least one mesenchymal marker and CD34, and/or enriching an MSC population (i.e., a relatively more heterogeneous MSC population) for MSC cells which co-express at least one mesenchymal marker and CD34, by means of suitable culturing conditions. This entails exposing said relatively more heterogeneous population of MSC (e.g., MSC cells isolated from a sample of a subject) to a haematopoietic growth factor and/or an angiogenic growth factor, preferably to a haematopoietic growth factor and an angiogenic growth factor, e.g., to one or more haematopoietic growth factors and/or one or more angiogenic growth factors.

Advantageously, the method may obtain and/or enrich MSC cells comprising expression of CD34 and one or more mesenchymal markers, such as preferably CD105, CD90 and/or CD73, also preferably at least CD105, from a starting or initial MSC cell population. Advantageously, the enriched-for MSC cells may lack expression of haematopoietic and/or endothelial markers, such as for example CD45, CD133, CD31, CD14 and/or CD19. Hence, in an embodiment the enriched-for MSC cells may comprise expression of CD34 and of one or more or preferably all of CD105, CD90 and CD73, also preferably at least CD105, and may lack the expression of one or more or preferably all of CD45, CD133, CD31, CD14 and CD19. Advantageously, the present method realises an increase in the proportion of MSC cells comprising co-expression of CD34 and one or more mesenchymal markers in an initial MSC population in the course of the application of the method (for example, in a non-limiting experiment the proportion of CD105-positive and CD-34 positive MSC cells increased respectively from 15% to 95% and from 1% to 59.4% during culture).

Advantageously, MSC cells expanded and/or enriched by exposing to haematopoietic and/or angiogenic growth factors as taught herein may display both adequate osteogenic properties (e.g., as demonstrated by ALP expression and staining) and beneficial pro-angiogenic properties (e.g., as demonstrated by vWF and VEGF expression and/or by capillary-like structure formation in a suitable assay).

Hence, also disclosed herein are MSC cells in general, and MSC cells co-expressing at least one mesenchymal marker and CD34 in particular, wherein said MSC cells display both osteogenic properties (as suitably but without limitation demonstrated by ALP expression, ALP enzymatic activity and/or ALP staining) and pro-angiogenic properties (as suitably but without limitation demonstrated by expression of vWF and/or VEGF, preferably vWF and VEGF, and/or by ability to organize into branched neo-vascular structures or pseudotubes in a suitable model such as a Matrigel model). Further contemplated are cell populations comprising such MSC cells.

Also provided are MSC cells obtainable or directly obtained by said methods of expanding or enriching MSC cells or cell populations using a haematopoietic growth factor and/or an angiogenic growth factor.

Another aspect relates to methods for differentiating in vitro the mesenchymal stem cells (MSC) co-expressing at least one mesenchymal marker and CD34 as defined in the preceding aspects, into bone-forming cells, such as for example osteoblasts or osteoprogenitors.

A further aspect provides bone-forming cells, such as for example osteoblasts or osteoprogenitors, obtainable by differentiating in vitro the mesenchymal stem cells (MSC) co-expressing at least one mesenchymal marker and CD34 as defined in the preceding aspects, into bone-forming cells.

As at least some of such bone-forming cells can maintain the relevant expression profile of the originating MSC cells, another aspect provides isolated bone-forming cells, such as for example osteoblasts or osteoprogenitors, characterised in that they co-express at least one mesenchymal marker and CD34.

Further disclosed is a cell population comprising isolated bone-forming cells co-expressing at least one mesenchymal marker and CD34. Hence, also disclosed is a cell population comprising isolated MSC co-expressing at least one mesenchymal marker and CD34 as taught herein and further comprising isolated bone-forming cells co-expressing at least one mesenchymal marker and CD34 as taught herein.

It shall be appreciated that the present invention also encompasses various manipulations of bone-forming cells and cell populations as taught above, such as bone-forming cells co-expressing at least one mesenchymal marker and CD34 and cell populations comprising such bone-forming cells, including inter alia culturing, maintaining, expanding, enriching (e.g., by sorting) and post-enrichment expanding of said bone-forming cells and cell populations.

Also disclosed is a method for obtaining bone-forming cells co-expressing at least one mesenchymal marker and CD34 comprising differentiating MSC cells co-expressing said at least one mesenchymal marker and CD34 to bone-forming cells.

Such bone-forming cells co-expressing at least one mesenchymal marker and CD34 may also be obtained by other methods. Hence, also disclosed is a method for obtaining bone-forming cells co-expressing at least one mesenchymal marker and CD34 comprising enriching or isolating from a population of bone-forming cells a subset of cells which co-express said at least one mesenchymal marker and CD34. An embodiment provides a method for obtaining bone-forming cells co-expressing at least one mesenchymal marker and CD34 comprising (a) isolating bone-forming cells from a sample of a subject or differentiating bone-forming cells from MSC cells isolated from a sample of a subject; (b) optionally enriching and/or expanding the bone-forming cells of (a); and (c) enriching or isolating from the bone-forming cells of (a) or (b) a subset of cells which co-express at least one mesenchymal marker and CD34.

A further aspect provides a method for in vitro expanding of isolated bone-forming cells, preferably of isolated bone-forming cells which co-express at least one mesenchymal marker and CD34 as taught herein, comprising exposing said bone-forming cells to a haematopoietic growth factor and/or an angiogenic growth factor, preferably to a haematopoietic growth factor and an angiogenic growth factor, e.g., to one or more haematopoietic growth factors and/or one or more angiogenic growth factors.

This method may also be adapted for obtaining from a bone-forming cell population (i.e., a relatively more heterogeneous bone-forming cell population) bone-forming cells which co-express at least one mesenchymal marker and CD34, and/or enriching a bone-forming cell population (i.e., a relatively more heterogeneous bone-forming cell population) for bone-forming cells which co-express at least one mesenchymal marker and CD34, by means of suitable culturing conditions. This entails in vitro exposing said relatively more heterogeneous population of bone-forming cells (e.g., bone-forming cells isolated from a sample of a subject or differentiated from MSC cells isolated from a sample of a subject) to a haematopoietic growth factor and/or an angiogenic growth factor, preferably to a haematopoietic growth factor and an angiogenic growth factor, e.g., to one or more haematopoietic growth factors and/or one or more angiogenic growth factors.

Advantageously, the method may obtain and/or enrich bone-forming cells comprising expression of CD34 and one or more mesenchymal markers, such as preferably CD105, CD90 and/or CD73, also preferably at least CD105, from a starting or initial bone-forming cell population. Advantageously, the enriched-for bone-forming cells may lack expression of haematopoietic and/or endothelial markers, such as for example CD45, CD133, CD31, CD14 and/or CD19. Hence, in an embodiment the enriched-for bone-forming cells may comprise expression of CD34 and of one or more or preferably all of CD105, CD90 and CD73, also preferably at least CD105, and may lack the expression of one or more or preferably all of CD45, CD133, CD31, CD14 and CD19. Advantageously, the present method realises an increase in the proportion of bone-forming cells comprising co-expression of CD34 and one or more mesenchymal markers in an initial bone-forming cell population in the course of the application of the method.

Advantageously, bone-forming cells expanded and/or enriched by exposing to haematopoietic and/or angiogenic growth factors as taught herein may display both adequate osteogenic properties (e.g., as demonstrated by ALP expression and staining) and beneficial pro-angiogenic properties (e.g., as demonstrated by vWF and VEGF expression and/or by capillary-like structure formation in a suitable assay).

Hence, also disclosed herein are bone-forming cells in general, and bone-forming cells co-expressing at least one mesenchymal marker and CD34 in particular, wherein said bone-forming cells display both osteogenic properties (as suitably but without limitation demonstrated by ALP expression, ALP enzymatic activity and/or ALP staining) and pro-angiogenic properties (as suitably but without limitation demonstrated by expression of vWF and/or VEGF, preferably vWF and VEGF, and/or by ability to organize into branched neo-vascular structures or pseudotubes in a suitable model such as a Matrigel model). Further contemplated are cell populations comprising such bone-forming cells.

Also provided are bone-forming cells obtainable or directly obtained by said methods of expanding or enriching bone-forming cells or cell populations using a haematopoietic growth factor and/or an angiogenic growth factor.

In an embodiment, the haematopoietic growth factor may include any growth factor having demonstrable haematopoietic activity as known in the art, such as, e.g., being capable of recruiting, inducing proliferation and/or stimulating haematopoietic cells. In an embodiment, the haematopoietic growth factor as intended throughout this specification is chosen from a group comprising or consisting of colony stimulating factor 2 (CSF2), CSF3, macrophage CSF (M-CSF), granulocyte monocytes CSF (GM-CSF), interferon (IFN) including inter alia IFN-alpha and IFN-gamma, tumour necrosis factor (TNF), and haematopoietically active cytokines such as inter alia interleukin 2 (IL2), IL4, IL17 and IL18. Preferably, the haematopoietic growth factor may be chosen from GM-CSF and IFN-gamma, more preferably may be IFN-gamma.

In an embodiment, the angiogenic growth factor may include any growth factor having demonstrable angiogenic activity as known in the art, such as, e.g., being capable of recruiting endothelial cells or inducing the formation of capillary structures by endothelial cells. In an embodiment, the angiogenic growth factor as intended throughout this specification is chosen from a group comprising or consisting of platelet-derived growth factor (PDGF) including inter alia PDGF aa, ab, bb, vascular endothelial growth factors (VEGF1 or 2), Von Willebrand factor (vWF), angiopoietin 1 or 2, fibroblast growth factors (FGF1, FGF-3, or other FGF factors; or an FGF factor other than FGF-1 and/or other than FGF-2) and erythropoietin (EPO). In another embodiment, the angiogenic growth factor may be chosen from a group comprising or consisting of PDGF, VEGF, vWF, angiopoietin 2 and EPO. Preferably, the angiogenic growth factor may be chosen from PDGF, FGF-1 and 3, more preferably may be PDGF or FGF-3, even more preferably may be PDGF.

Preferably, in addition to said haematopoietic growth factor and/or angiogenic growth factor the MSC or bone-forming cells may be exposed, preferably concurrently exposed, to FGF-2 to further stimulate the maintenance, expansion, obtaining, enrichment and/or osteogenic differentiation of said cells.

Hence, in a preferred embodiment expanding MSC or bone-forming cells, such as for example MSC or bone-forming cells comprising expression of CD34 and one or more mesenchymal markers as taught herein, may comprise exposing said MSC or bone-forming cells to one or more growth factors chosen from GM-CSF, IFN-gamma, PDGF, FGF-1 and FGF-3; for example to one or more of GM-CSF and IFN-gamma and/or to one or more of PDGF, FGF-1 and FGF-3; for example to one or more of GM-CSF and IFN-gamma and to one or more of PDGF, FGF-1 and FGF-3. Optionally in these embodiments the cells may be also exposed, preferably concurrently exposed, to FGF-2. In a particularly preferred embodiment expanding MSC or bone-forming cells, such as for example MSC or bone-forming cells comprising expression of CD34 and one or more mesenchymal markers as taught herein, may comprise exposing said MSC or bone-forming cells to IFN-gamma. This treatment noticeably enhances both osteogenic and pro-angiogenic characteristics of the so-treated cells.

In another preferred embodiment enriching for MSC or bone-forming cells comprising expression of CD34 and one or more mesenchymal markers as taught herein from an initial MSC or bone-forming cells population, may comprise exposing said initial MSC or bone-forming cells population to one or more growth factors chosen from GM-CSF, IFN-gamma, PDGF, FGF-1 and FGF-3; for example to one or more of GM-CSF and IFN-gamma and/or to one or more of PDGF, FGF-1 and FGF-3; for example to one or more of GM-CSF and IFN-gamma and to one or more of PDGF, FGF-1 and FGF-3. Optionally in these embodiments the cells may be also exposed, preferably concurrently exposed, to FGF-2. In a particularly preferred embodiment enriching for MSC or bone-forming cells comprising expression of CD34 and one or more mesenchymal markers as taught herein from an initial MSC or bone-forming cells population may comprise exposing said MSC or bone-forming cells to IFN-gamma. This treatment noticeably enhances both osteogenic and pro-angiogenic characteristics of the so-treated cells.

A further aspect provides a pharmaceutical composition comprising: mesenchymal stem cells (MSC) co-expressing at least one mesenchymal marker and CD34 as defined in the preceding aspects and/or the bone-forming cells as defined in the preceding aspects such as bone-forming cells co-expressing at least one mesenchymal marker and CD34, and one or more pharmaceutically acceptable carrier/excipient. The pharmaceutical composition may comprise a cell population comprising said MSC and/or bone-forming cells, and one or more pharmaceutically acceptable carrier/excipient.

A process for preparing the pharmaceutical formulation is also provided, comprising: admixing the mesenchymal stem cells (MSC) co-expressing at least one mesenchymal marker and CD34 as defined in the preceding aspects and/or the bone-forming cells as defined in the preceding aspects such as bone-forming cells co-expressing at least one mesenchymal marker and CD34, or a cell population comprising such MSC and/or bone-forming cells, with said one or more pharmaceutically acceptable carrier/excipient.

The cell products of the invention are particularly suitable for prophylactic and therapeutic treatments of bone-related disorders. Thus, further aspects relate to:

the mesenchymal stem cells (MSC) co-expressing at least one mesenchymal marker and CD34 as defined in the preceding aspects, or the bone-forming cells as defined in the preceding aspects such as bone-forming cells co-expressing at least one mesenchymal marker and CD34, or the cell populations or pharmaceutical compositions comprising the cells as defined above, for use in the treatment of a bone-related disorder;

use of the mesenchymal stem cells (MSC) co-expressing at least one mesenchymal marker and CD34 as defined in the preceding aspects, or the bone-forming cells as defined in the preceding aspects such as bone-forming cells co-expressing at least one mesenchymal marker and CD34, or the cell populations comprising the cells as defined above, for the manufacture of a medicament for the treatment of bone-related disorders;

a method for treating a bone-related disorder in a subject in need of such treatment, comprising administering to said subject a therapeutically or prophylactically effective amount of the mesenchymal stem cells (MSC) co-expressing at least one mesenchymal marker and CD34 as defined in the preceding aspects, or the bone-forming cells as defined in the preceding aspects such as bone-forming cells co-expressing at least one mesenchymal marker and CD34, or the cell populations or pharmaceutical compositions comprising the cells as defined above.

The invention also provides an arrangement comprising a surgical instrument adapted for administration of a composition to a subject, such as for example systemically or at a site of bone lesion, and further comprising any of the cells, cell populations or pharmaceutical compositions defined above.

In any of above aspects and embodiments, the at least one mesenchymal marker may be preferably chosen from CD105, CD90 and CD73, more preferably it may be CD90 or CD105. Particularly preferably, the at least one mesenchymal marker may be CD105, i.e., the MSC or bone-forming cells as taught herein may co-express at least CD105 and CD34.

In some embodiments of any of the above aspects, the cells (MSC cells; bone-forming cells) are of human origin. Preferably, the MSC may originate from bone marrow.

These and further aspects and embodiments are described in the following sections and in the claims.

DETAILED DESCRIPTION OF THE INVENTION

Figure 1:
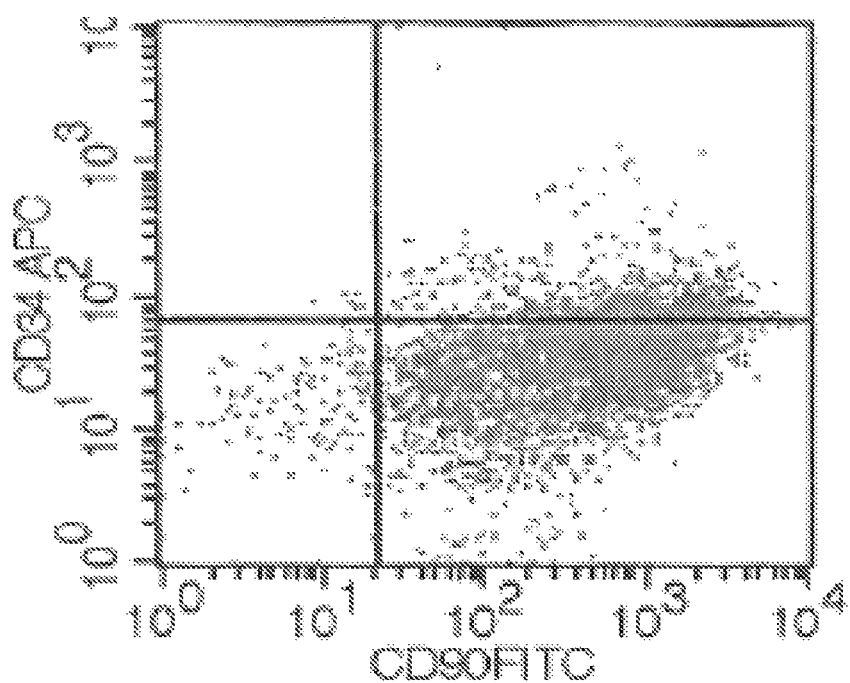
FIG. 1 illustrates dual-colour flow cytometric analysis of CD90 (FITC) and CD34 (APC) expression. The dot plot histogram represents 5000 events collected as list mode data.

As used herein, the singular forms "a", "an", and the include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The term "stem cell" refers generally to an unspecialised or relatively less specialised and proliferation-competent cell, which is capable of self-renewal, i.e., can proliferate without differentiation, and which or the progeny of which can give rise to at least one relatively more specialised cell type. The term encompasses stem cells capable of substantially unlimited self-renewal, i.e., wherein the progeny of a stem cell or at least part thereof substantially retains the unspecialised or relatively less specialised phenotype, the differentiation potential, and the proliferation capacity of the mother stem cell, as well as stem cells which display limited self-renewal, i.e., wherein the capacity of the progeny or part thereof for further proliferation and/or differentiation is demonstrably reduced compared to the mother cell. By means of example and not limitation, a stem cell may give rise to descendants that can differentiate along one or more lineages to produce increasingly relatively more specialised cells, wherein such descendants and/or increasingly relatively more specialised cells may themselves be stem cells as defined herein, or even to produce terminally differentiated cells, i.e., fully specialised cells, which may be post-mitotic.

The term "adult stem cell" as used herein refers to a stem cell present in or obtained from (such as isolated from) an organism at the foetal stage or after birth.

The term "mesenchymal stem cell" or "MSC" as used herein refers to an adult, mesoderm-derived stem cell that is capable of generating cells of mesenchymal lineages, typically cells of two, preferably of three or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. Commonly, but without limitation, a cell may be considered MSC if it is capable of forming cells of each of the adipocytic, chondrocytic and osteocytic lineages, using standard, art-accepted differentiation conditions and cellular phenotype evaluation methods, e.g., as described in Pittenger et al. 1999 (Science 284: 143-7) or Barberi et al. (PLoS Med 2: e161, 2005). MSC cells may be isolated from, e.g., bone marrow, blood, umbilical cord, placenta, foetal yolk sac, dermis especially foetal and adolescent skin (Young et al. 2001. Anat Rec 264: 51-62), periosteum, and adipose tissue (Zuk et al. 2001. Tissue Eng 7: 211-28). Human MSC, their isolation, in vitro expansion, and differentiation, have been described in, e.g., Pittenger et al. 1999 (supra), U.S. Pat. No. 5,486,359; U.S. Pat. No. 5,811,094; U.S. Pat. No. 5,736,396; U.S. Pat. No. 5,837,539; or U.S. Pat. No. 5,827,740.

The term also encompasses MSC obtained from bone marrow, which are commonly referred to as "bone marrow stromal cells" or "BMSC". A sample of bone marrow for isolation of BMSC may be acquired, e.g., from iliac crest, femora, tibiae, spine, rib or other medullar spaces.

In a preferred embodiment MSC or MSC populations as used herein may originate from bone marrow, e.g., may be isolated and optionally expanded from a bone marrow sample. MSC and MSC populations originated from bone-marrow can have characteristics (e.g., marker profile, function, expansion, differentiation, etc.) different from and/or favourable over MSC originated from other tissues, such as without limitation may more efficiently and/or more controllably differentiate into bone-forming cells.

The terms MSC and BMSC also encompass the progeny of MSC or BMSC, e.g., progeny obtained by in vitro or ex vivo propagation of MSC or BMSC obtained from a biological sample of a subject.

The term "isolating" with reference to a particular component denotes separating that component from at least one other component of a composition from which the former component is thereby "isolated". The term "isolated" used in relation to any cell, group of cells or a cell population also implies that such cell, group of cells or cell population does not form part of an animal or human body.

Cells as disclosed herein, in particular MSC cells or bone-forming cells, co-express (i.e., are positive for) at least one mesenchymal marker and CD34. Throughout this specification "co-express" intends to cover the meaning "comprising co-expression of", such that the cells can express other markers in addition to the particular recited markers characterising the cells.

Where a cell is said to be positive for a particular marker, this means that a skilled person will conclude the presence or evidence of a distinct signal, e.g., antibody-detectable or detection by reverse transcription polymerase chain reaction, for that marker when carrying out the appropriate measurement, compared to suitable controls. Where the method allows for quantitative assessment of the marker, positive cells generate a signal that is significantly different from and higher or stronger than the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of cell-specific markers can be detected using any suitable immunological technique known in the art, such as immuno-cytochemistry or affinity adsorption, Western blot analysis, FACS, ELISA, etc., or by any suitable biochemical assay of enzyme activity, or by any suitable technique of measuring the quantity of the marker mRNA, e.g., Northern blot, semi-quantitative or quantitative RT-PCR, etc.

Nucleic and amino acid sequence data for marker proteins listed in this disclosure are generally known and can be obtained from public databases such as, among others, from the NIH "Protein Reviews on the Web" database (http://mpr.nci.nih.gov/prow/), the NIH "Entrez Gene" database (http://www.ncbi.nlm.nih.gov/sites/entrez?db=gene) or the Uniprot/Swissprot database (http://www.expasy.org/). Suitable detection reagents and methods for said markers can be designed either on the basis of such sequence information or, more commonly, are available commercially (e.g., labelled monoclonal antibody reagents).

By example and without limitation, referring to entries in the above databases in that order, human CD34 antigen is found under "CD34", Gene ID 947, and acc. number P28906 (seq. version 2, entry version 74) (also Simmons et al. 1992. J Immunol 148: 267-271; Civin et al. 1984. J Immunol 133: 157); human CD105 antigen (also known as endoglin) is found under "CD105", Gene ID 2022 and acc. number P17813 (seq. version 2, entry version 91) (also Bellon et al. 1993. Eur J Immunol 23: 2340); human CD90 antigen (also known as Thy-1 membrane glycoprotein) is found under "CD90", Gene ID 7070 and acc. number PO4216 (seq. version 2, entry version 94) (also Cell surface Thy-1, ed. A F Reif and M Schlesinger, 1989, Marcel Dekker Inc., New York); and human CD73 antigen (also known as ecto-5'-nucleotidase, EC 3.1.3.5) is found under "CD73", Gene ID 4907 and acc. number P21589 (seq. version 1, entry version 87) (also Thomson et al. 1990. Tissue Antigens 35: 9).

Example available antibody reagents for detection of CD34 include inter alia monoclonal antibodies 6A6, 7E10 and 4H11, of CD105 include inter alia monoclonal antibodies 44G4, 1G2, E-9 and GRE (Letarte et al. 1995. In: Leukocyte Typing V, ed. SF Schlossman et al., Oxford University Press, Oxford, p. 1756-1759), of CD90 include inter alia monoclonal antibody 5E10 (Craig et al. 1993. J Exp Med 177: 1331), and of CD73 include inter alia monoclonal antibodies 1E9 and 7G2 (Thompson et al. 1990, supra) and 4G4 (Airas et al. 1993. J Immunol 151: 4228).

In an embodiment, the at least one mesenchymal marker is chosen from CD105, CD90 and CD73. Preferably, the at least one mesenchymal marker is CD90 or CD105, more preferably the at least one mesenchymal marker is CD105. The invention contemplates cells, in particular MSC cells or bone-forming cells, which co-express CD105 and CD34, cells which co-express CD90 and CD34, as well as cells which co-express CD73 and CD34. Also covered are cells, in particular MSC cells or bone-forming cells, which co-express any two or all three of CD105, CD90 and CD73, with CD34, such as, e.g., cells co-expressing at least CD105 and CD90 with CD34, or cells co-expressing at least CD105 and CD73 with CD34.

As shown in the examples, cells of the above marker profile may also co-express alkaline phosphatase (ALP). Hence, also provided are cells, in particular MSC cells or bone-forming cells as disclosed herein, co-expressing at least one mesenchymal marker and CD34, and further expressing ALP, more preferably ALP of the bone-liver-kidney type (ALPL). Exemplary human ALP of the latter type is described in Weiss et al. 1986 (PNAS 83: 7182-7186) and under Uniprot/Swissprot acc. number P05186 (seq. version 4, entry version 110). ALP may be detected essentially as explained above, making use its known sequence and commercially available detection reagents such as labelled antibodies. Enzyme-based assays using substrates such as for example 4-methylumbelliferyl phosphate (Fernley et al. 1965. Biochem J. 97: 95-103) or p-nitrophenylphosphate are also well-known.

MSC cells of the above marker profile may typically also display other attributes of mesenchymal cells. For example, the MSC cells may further express one, more or all of mesenchymal markers chosen from CD106 (VCAM), CD166 (ALCAM), CD29, CD44, CD54 and GATA-4. The MSC cells may further display certain morphological features, such as any one or more of adherence to tissue culture plastic; growth in monolayers; and mononuclear ovoid, stellate or spindle shape with round to oval nuclei having prominent nucleoli.

The term "bone-forming cells" as used herein generally refers to cells capable of contributing to the formation of bone material and/or bone matrix, an particularly denotes isolated cells or cell populations which have partly or fully progressed along osteogenic differentiation pathway. Without limitation, bone-forming cells particularly encompass osteoprogenitors, osteoblasts, osteocytes and other cell types of the osteogenic lineage as known in the art.

A skilled person thus generally appreciates the bounds of the term "bone-forming cells" as intended herein. Nevertheless, by means of further guidance and not limitation the present bone-forming cells may display any one, more or all following characteristics:

a) the cells comprise expression of alkaline phosphatase (ALP), more specifically ALP of the bone-liver-kidney type;
b) the cells comprise expression of any one or more of pro-collagen type 1 amino-terminal propeptide (P1NP), osteonectin (ON), osteopontin (OP), osteocalcin (OCN) and bone sialoprotein (BSP);
c) the cells show evidence of ability to mineralize the external surroundings, or synthesize calcium-containing extracellular matrix (e.g., when exposed to osteogenic medium; see Jaiswal et al. 1997. J Cell Biochem 64: 295-312). Calcium accumulation inside cells and deposition into matrix proteins can be conventionally measured for example by culturing in $^{45}Ca^{2+}$, washing and re-culturing, and then determining any radioactivity present inside the cell or deposited into the extracellular matrix (U.S. Pat. No. 5,972,703), or using an Alizarin red-based mineralization assay (see, e.g., Gregory et al. 2004. Analytical Biochemistry 329: 77-84);
d) the cells substantially do not differentiate towards any one of, and preferably towards neither of cells of adipocytic lineage (e.g., adipocytes) or chondrocytic lineage (e.g., chondrocytes). The absence of differentiation towards such cell lineages may be tested using standard differentiation inducing conditions established in the art (e.g., see Pittenger et al. 1999. Science 284: 143-7), and assaying methods (e.g., when induced, adipocytes typically stain with oil red O showing lipid accumulation; chondrocytes typically stain with alcian blue or safranin O). Substantially lacking propensity towards adipogenic and/or chondrogenic differentiation may typically mean that less than 50%, or less than 30%, or less than 5%, or less than 1% of the tested cells would show signs of adipogenic or chondrogenic differentiation when applied to the respective test.

In an embodiment the bone-forming cells may display all characteristics listed under a), c) and d) above.

Further contemplated are any cell populations, comprising the isolated MSC cells or bone-forming cells as disclosed herein, or comprising both said cell types. Said MSC cells or bone-forming cells as disclosed herein, or both said cell types taken together, may constitute at least 2%, preferably at least 5%, such as at least 10%, more preferably at least 20%, such as at least 30%, even more preferably at least 40%, such as at least 50%, or very preferably at least 60%, such as at least 70%, at least 80%, at least 90% or up to 100% of cells present in such cell populations.

Preferably, MSC cells or bone-forming cells as disclosed herein, or cell populations comprising such, are of animal origin, more preferably of non-human mammal or human origin, even more preferably of human origin.

MSC cells co-expressing at least one mesenchymal marker and CD34, and optionally any additional marker of interest, as disclosed herein may be obtained by methods which are known per se.

For example, conventional methods allow to isolate and optionally expand MSC or BMSC cells from biological samples of subjects.

The terms "biological sample" or "sample" as used herein generally refer to a sample obtained from a biological source, e.g., from an organism, organ, tissue or cell culture, etc. A biological sample of an animal subject, such as non-human mammal or human subject, refers to a sample removed from said subject and comprising cells thereof. Methods of obtaining biological samples of subjects are well known in the art, e.g., tissue biopsy or drawing blood or bone marrow. A useful sample of a subject comprises MSC or BMSC cells thereof. Such sample may be typically obtained from bone marrow, e.g., from iliac crest, femora, tibiae, spine, rib or other medullar spaces of a subject. Further useful biological sample comprising MSC may be derived, e.g., from, blood, umbilical cord, placenta, foetal yolk sac, skin, periosteum, or adipose tissue of a subject.

It has been described that MSC or BMSC can be isolated and expanded from bone marrow or other sources by selecting and culturing there from cells which can adhere to a substrate surface, in particular to tissue culture plastic surface. Protocols based on this principle are detailed in Pittenger et al. 1999 (supra) and related patent documents mentioned elsewhere in this specification, as well as reviewed in Alhadlaq & Mao 2004 (Stem Cells Dev 13: 436-48). These protocols are applicable herein.

Cells co-expressing the desired marker proteins can be selected, enriched or isolated from the general population of isolated and optionally expanded MSC or BMSC cells by methods known per se, such as, for example, using fluorescence activated cell-sorting (FACS), magnetic-activated cell sorting (MACS) or affinity-based technologies inter alia affinity chromatography. Live cells having a desired expression profile are allowed to bind with reagents (most commonly immunological reagents such as, e.g., monoclonal antibodies) specific for the respective markers, wherein said reagents are in turn modified (e.g., by a fluorophore, or by immobilisation on magnetic particles or another type of stationary phase), such as to facilitate for selection or capture of cells bound by said reagents from cells not so bound.

For general guidance on these methods, refer inter alia to Flow Cytometry and Cell Sorting, 2nd ed., by Andreas Radbruch (ed.), Springer 1999 (ISBN 3540656308); In Living Color: Protocols in Flow Cytometry and Cell Sorting, 1st ed., by R A Diamond and S Demaggio (eds.), Springer 2000 (ISBN 3540651497); Flow Cytometry Protocols (Methods in Molecular Biology), 2nd ed., by T S Hawley and R G Hawley (eds.), Humana Press 2004 (ISBN 1588292355); Affinity Separations: A Practical Approach, P Matejtschuk (ed.), Oxford University Press, 1997 (ISBN 0199635501); and Dainiak et al. 2007. Adv Biochem Eng Biotechnol 106: 1-18.

The inventors also realised advantageous conditions for in vitro expanding of MSC cells or bone-forming cells, and particularly for in vitro expanding of the isolated MSC cells or bone-forming cells as defined herein co-expressing at least one mesenchymal marker and CD34, which may also be adapted for enriching the MSC cells or bone-forming cells co-expressing at least one mesenchymal marker and CD34 from a relatively more heterogeneous MSC or bone-forming cell population.

The term "enriching" as used in this context refers to increasing the relative proportion of a desired cell type or cell phenotype in a population of cells. For example, from a starting cell population subjected to enrichment, said CD34 positive MSC cells or bone-forming cells may be enriched to at least 2%, preferably at least 5%, such as at least 10%, more preferably at least 20%, such as at least 30%, even more preferably at least 40%, such as at least 50%, or very preferably at least 60%, such as at least 70%, at least 80%, at least 90% or up to 100% of cells present in a resulting cell population. The MSC cells or MSC cell population, or the bone-forming cells or bone-forming cell population, are exposed to a haematopoietic growth factor, or to an angiogenic growth factor, or to a combination of a haematopoietic and angiogenic growth factor, the latter combination achieving a synergic effect on the cell expansion or enrichment. The haematopoietic and angiogenic growth factor may be contacted with the cells simultaneously or sequentially in any order, preferably simultaneously. Advantageously, the cells may be exposed, preferably simultaneously exposed, to FGF-2 to further enhance their expansion and/or enrichment.

In an embodiment, the haematopoietic growth factor is chosen from a group comprising or consisting of colony stimulating factor 2 (CSF2), CSF3, macrophage CSF (M-CSF), granulocyte monocytes CSF (GM-CSF), interferon (IFN) including IFN-gamma, tumour necrosis factor (TNF), and haematopoietically active cytokines such as inter alia interleukin 2 (IL2). More preferably, the haematopoietic growth factor is chosen from GM-CSF and IFN-gamma, even more preferably may be IFN-gamma. In an embodiment, the angiogenic growth factor is chosen from a group comprising or consisting of platelet-derived growth factor (PDGF), vascular endothelial growth factors (VEGF1 or 2), Von Willebrand factor (vWF), angiopoietin 2, fibroblast growth factors (FGF1, FGF3, or other FGF factors) and erythropoietin (EPO). More preferably, the angiogenic growth factor is chosen from PDGF, FGF-1 and FGF-3, even more preferably PDGF and FGF-3, still more preferably may be PDGF.

The term "exposing" as used herein means bringing together, i.e., contacting, either directly or indirectly, one or more molecules, components or materials with another, thereby facilitating interactions there between. Typically, the growth factor(s) may be contacted with the cells by means of their inclusion in the media, in which said cells are cultured. Media, disposables and conditions of cell culture applicable herein may be generally as known in the art, such as in the art of propagating and differentiating MSC, BMSC and bone-forming cells.

Bone-forming cells may be obtained by differentiation from isolated MSC cells as known in the art. In an example, the method of WO 2007/093431 may be used, wherein isolated MSC cells are cultured in the presence of serum or plasma and basic fibroblast growth factor (FGF-2). In another example, osteogenic lineage cells may be obtained by differentiating MSC cells in osteogenic medium as described by Pittenger et al. 1999 (supra) and Jaiswal et al. 1997 (supra). Optionally, a conventional osteogenic medium may be supplemented by FGF-2. Bone-forming cells can also be directly isolated and cultured from trabecular bone as described by Skjodt et al. 1985 (J Endocrinol 105: 391-6).

In an embodiment, the bone-forming cells may be differentiated from isolated MSC cells which co-express at least one mesenchymal marker and CD34. In such case, the so-obtained population of bone-forming cells may be enriched for bone-forming cells co-expressing said at least one mesenchymal marker and CD34. In another example, bone-forming cells may be obtained from MSC cells which have not been enriched for cells co-expressing at least one mesenchymal marker and CD34, or may be directly isolated from a subject. In such case, the so-obtained population of bone-forming cells would generally not be enriched for bone-forming cells co-expressing said at least one mesenchymal marker and CD34.

In any of these situations, techniques as described above for MSC cells (such as, e.g., FACS, MACS or affinity-based technologies) can be used analogously to select, enrich or isolate bone-forming cells co-expressing said at least one mesenchymal marker and CD34, from a relatively more heterogeneous population of bone cells. Bone-forming cells co-expressing said at least one mesenchymal marker and CD34 may also be enriched using a haematopoietic and/or angiogenic growth factor as taught in this specification.

In the context of the various aspects of the invention, the term "bone-related disorder" refers to any type of bone disease, the treatment of which may benefit from the administration of osteogenic lineage or bone-forming cells, e.g., osteoprogenitors, osteoblasts or osteocytes, to a subject having the disorder. In particular, such disorders may be characterised, e.g., by decreased bone formation or excessive bone resorption, by decreased number, viability or function of osteoblasts or osteocytes present in the bone, decreased bone mass in a subject, thinning of bone, compromised bone strength or elasticity, etc.

By way of example and not limitation the term encompasses local or systemic disorders, such as, any type of osteoporosis or osteopenia, e.g., primary, postmenopausal, senile, corticoid-induced, any secondary, mono- or multisite osteonecrosis, any type of fracture, e.g., non-union, mal-union, delayed union fractures or compression, conditions requiring bone fusion (e.g., spinal fusions and rebuilding), maxillo-facial fractures, bone reconstruction, e.g., after traumatic injury or cancer surgery, cranio-facial bone reconstruction, osteogenesis imperfecta, osteolytic bone cancer, Paget's Disease, endocrinological disorders, hypophosphatemia, hypocalcemia, renal osteodystrophy, osteomalacia, adynamic bone disease, rheumatoid arthritis, hyperparathyroidism, primary hyperparathyroidism, secondary hyperparathyroidism, periodontal disease, Gorham-Stout disease and McCune-Albright syndrome.

The MSC, BMSC and bone-forming cells and populations comprising such as described by the invention find various uses, in particular in the fields of research, prevention and therapy of bone-related disorders.

In an aspect, the cells or cell populations may be used for producing bone matrix in vitro. Said bone matrix may be employed, e.g., in conjunction with or without the cells or cell populations, in treatment of bone related diseases.

Introduction of the present cells or cell populations to subjects can be useful in the treatment of bone fractures and bone-related disorders in said subjects. The terms "subject" or "patient" refer preferably to animals, more preferably warm-blooded animals, yet more preferably vertebrates, and even more preferably mammals specifically including humans and non-human mammals, that have been the object of treatment, observation or experiment. The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof.

The present treatments are particularly to be given to subjects in need thereof, which phrase includes subjects that would benefit from treatment of a given condition, such as bone fracture or a bone-related disorder. Such subjects may include, without limitation, those that have been diagnosed with said condition, those prone to develop said condition and/or those in whom said condition is to be prevented.

The terms "treat" or "treatment" encompass both the therapeutic treatment of an already developed disorder, such as the therapy of an already developed bone-related disorder, as well as prophylactic or preventative measures, wherein the aim is to prevent or lessen the chances of incidence of an undesired affliction, such as to prevent the chances of contraction and progression of a bone-related disorder. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or disorder being treated. Methods are known in the art for determining therapeutically and prophylactically effective doses.

The treatment may employ autologous (i.e., cells derived from the subject to be treated), allogeneic (i.e., cells derived from subject(s) other than the subject to be treated, but belonging to the same species) or xenogenic (i.e., cells derived from subject(s) belonging to species other than the subject to be treated) MSC, BMSC or bone-forming cells or cell populations as defined herein.

Envisaged are in particular treatments of human subjects using human autologous or allogeneic MSC, BMSC or bone-forming cells or cell populations as obtained herein.

Suitably, the herein derived MSC, BMSC or bone-forming cells and cell populations may be formulated into and administered as pharmaceutical compositions.

Pharmaceutical compositions will typically comprise the MSC, BMSC or bone-forming cells or cell populations of the invention as the active ingredient, and one or more pharmaceutically acceptable carrier/excipient. As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active substances is well known in the art. Such materials should be non-toxic and should not interfere with the activity of the cells.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin, which may increase the viability of the cells.

The pharmaceutical compositions may comprise further components useful in the repair of bone wounds and defects. For example, such components may include without limitation bone morphogenetic proteins, bone matrix (e.g., bone matrix produced in vitro by cells of the invention or by other methods), hydroxyapatite/tricalcium phosphate particles (HA/TCP), gelatine, poly-lactic acid, poly-lactic glycolic acid, hyaluronic acid, chitosan, poly-L-lysine, and collagen. For example, the osteoblastic cells may be combined with demineralised bone matrix (DBM) or other matrices to make the composite osteogenic (bone forming in it own right) as well as osteo-inductive. Similar methods using autologous bone marrow cells with allogeneic DBM have yielded good results (Connolly et al. 1995. Clin Orthop 313: 8-18).

The pharmaceutical composition can further include or be co-administered with a complementary bioactive factor such as a bone morphogenic protein, such as BMP-2, BMP-7 or BMP-4, or any other growth factor. Other potential accompanying components include inorganic sources of calcium or phosphate suitable for assisting bone regeneration (WO 00/07639). If desired, cell preparation can be administered on a carrier matrix or material to provide improved tissue regeneration. For example, the material can be a granular ceramic, or a biopolymer such as gelatine, collagen, osteonectin, fibrinogen, or osteocalcin. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997).

Alternatively or in addition, the present cells may be stably or transiently transformed with a nucleic acid of interest prior to introduction into the bone lesion, e.g., a surgery or fracture site, of the subject. Nucleic acid sequences of interest include, but are not limited to those encoding gene products that enhance the growth, differentiation and/or mineralization of osteoblasts. For example, an expression system for BMP-2, can be introduced in a stable or transient fashion for the purpose of treating non-healing fractures or osteoporosis. Methods of cell transformation are known to those skilled in the art.

In a further aspect, the invention relates to an arrangement comprising a surgical instrument for administration of a composition to a subject, such as for example systemically, topically or at a site of bone lesion, and further comprising the cells or cell populations of the invention, or a pharmaceutical composition comprising said cells or cell populations, wherein the arrangement is adapted for administration of the pharmaceutical composition for example systemically, topically or at the site of bone lesion. For example, a suitable surgical instrument may be capable of injecting a liquid composition comprising cells of the present invention, such as systemically or at the site of bone lesion.

The cells or cell populations can be administered in a manner that permits them to graft or migrate to the intended tissue site and reconstitute or regenerate the functionally deficient area. Administration of the composition will depend on the musculoskeletal site being repaired. For example, osteogenesis can be facilitated in concordance with a surgical procedure to remodel tissue or insert a split, or a prosthetic device such as a hip replacement.

In other circumstances, invasive surgery will not be required, and the composition can be administered by injection or (e.g., for repair of the vertebral column) using a guidable endoscope.

In an embodiment the pharmaceutical cell preparation as defined above may be administered in a form of liquid composition. In embodiments, the cells or pharmaceutical composition comprising such can be administered systemically, topically or at a site of lesion.

In another embodiment, the cells or cell populations may be transferred to and/or cultured on suitable substrate to provide for implants. The substrate on which the cells can be applied and cultured can be a metal, such as titanium, cobalt/chromium alloy or stainless steel, a bioactive surface such as a calcium phosphate, polymer surfaces such as polyethylene, and the like. Although less preferred, siliceous material such as glass ceramics, can also be used as a substrate. Most preferred are metals, such as titanium, and calcium phosphates, even though calcium phosphate is not an indispensable component of the substrate. The substrate may be porous or non-porous.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating said support with a liquid suspension containing said cells. The impregnated supports obtained in this way can be implanted in a human subject. Such impregnated supports can also be re-cultured by immersing them in a liquid culture medium, prior to being finally implanted.

The three-dimensional solid support needs to be biocompatible so as to enable it to be implanted in a human. It can be of any suitable shape such as a cylinder, a sphere, a plate, or a part of arbitrary shape. Of the materials suitable for the biocompatible three-dimensional solid support, particular mention can be made of calcium carbonate, and in particular aragonite, specifically in the form of coral skeleton, porous ceramics based on alumina, on zirconia, on tricalcium phosphate, and/or hydroxyapatite, imitation coral skeleton obtained by hydrothermal exchange enabling calcium carbonate to be transformed into hydroxyapatite, or else apatite-wollastonite glass ceramics, bioactive glass ceramics such as Bioglass™ glasses.

The above aspects and embodiments are further supported by the following non-limiting examples.

The examples demonstrate the isolation of a new population subset of osteoprogenitor cells derived from mesenchymal stromal cells co-expressing high levels of CD34 (haemato-angiogenic characters) and CD105 (mesenchymal character), with enhanced bone formation properties and pro-angiogenic properties. This population accounts for less than 1% of normally expanded mesenchymal stromal cells. However, this population can successfully be enriched by a factor of up to 90 by dual cell sorting and/or by culture under in special conditions. Such an enriched CD105/CD34+ cell population (e.g., for up to 5 to 50%) is of outstanding interest for treatment of bone diseases as this enriched population has significantly higher proliferation potential and significantly higher bone reconstruction properties. In addition, their angiogenic (CD34+) properties add to the treatment benefits as a combination of revascularization induction and bone reconstruction may be preferred.

Example 1

Isolation and culture of bone marrow MSC. 100 ml of heparinized bone marrow (BM) was obtained from iliac crest of patients or from healthy volunteers. BM was mixed with phosphate-buffered saline (PBS, 2v:v) and layered on density gradient Ficoll solution. After centrifugation, mononuclear cells were harvested from the interface and washed twice in PBS. The cells were resuspended in DMEM medium supplemented with 20% plasma, optionally supplemented with FGF-2. The cells were plated at $1 \times 10^7$ cells/175 cm$^2$ flasks (tested range $1 \times 10^5$-$1 \times 10^9$) and maintained in a 37° C. humidified atmosphere containing 5% CO2. The cells were allowed to attach for 1 to 4 days prior to an initial medium change, and subsequently cultured for time intervals as specified below.

Isolation of CD34 positive cells. After 14 days of standard mesenchymal culture (DMEM and plasma at 20%), approximately $1 \times 10^8$ cells were harvested and maintained in PBS. The whole cell population was then labelled with an APC-labelled anti-CD34 monoclonal antibody for 1 h at room temperature. After a washing step by PBS, the cells are sedimented by centrifugation and resuspended in 1 ml of cold, degasses sorting buffer.

Purification of the cells was performed on a Becton Dickinson Immunocytometry system. The cells were sorted using the parameters of green fluorescence at 680 nm and drops containing fluorescent cells are then collected in sterile microcentrifuge tubes (Fisher scientific), sedimented by centrifugation and immediately seeded in appropriated flasks.

Enrichment by culture. MSC cells were detached at day 28 using trypsin solution for 1-5 min at 37° C. The cells were counted and plated at $1 \times 10^6$ cells/175 cm$^2$ for another week of culture in the same standard conditions with or without growth factors as specified in the examples.

Phenotype analysis. Immunobiological cell surface markers were analyzed by flow cytometry. Cells were incubated with the following labelled monoclonal antibodies: CD105, CD90 and CD73, as well as CD34 for 15 min and then washed with PBS before being centrifuged and resuspended in 0.3 ml PBS.

ALP staining. Cells were stained for ALP detection on day 28 or 35. Cells were washed twice with PBS, then fixed in 60% citrate buffered acetone for 30 seconds at room temperature, and then rinsed again with distilled water for 45 seconds. Cells were then stained with a Fast Blue RR/Naphtol AS-MX phosphate solution for 30 minutes at room temperature, and in the dark. Cells were washed with distilled water for 2 minutes, and then counterstained in Mayer's Haematoxylin solution for 10 minutes. Finally, cells were washed in distilled water for 3 minutes.

Mineralization assay. Cells from culture were recovered at day 28 or 35 by incubation with trypsin and plated at 60 to 120 000 cells/well in 6-wells plate in the expansion medium (12 500 cells/cm$^2$). The next day, the medium is replaced by 2.5 ml osteogenic medium. The cells are cultured for 2, 3 or 4 weeks. The medium is replaced every 3-4 days. After 2 weeks of culture, cells were fixed in 3.7% formaldehyde/PBS and stained by alizarin red.

Network formation assay. A Matrigel tube formation assay was performed to assess the ability of the cell population to form a network of capillary-like structures. Briefly, 24-well culture plates were coated with 10 μl (3.5 mg/ml) of pure Growth Factor-reduced Matrigel (BD Matrigel Basement Membrane Matrix, BD Biosciences, Erembodegem-Aalst, Belgium) per well according to manufacturer's instructions, and then allowed to polymerize for 30 minutes at 37° C. A total of $30.10^3$ cells/well were seeded on Matrigel and incubated for 6 hours at 37° C. After washing, network and tube formation were observed using an inverted phase-contrast microscope.

Media

Dexamethasone Dilution:

Dex1 ($5.10^{-4}$M): 2 μl dexamethasone stock ($5.10^{-2}$M)+198 μl αMEM

Dex2 ($10^{-6}$M): 2 μl Dex1 ($5.10^{-4}$M)+998 μl αMEM

Osteogenic medium (40 ml)

|  | Volume | Final conc. |
|---|---|---|
| αMEM | 31 ml | / |
| FCS | 6 ml | 15% |
| PenStrepGlu (100×) | 400 μl | 1× |
| Dexameth. (Dex2) | 400 μl | $10^{-8}$M |
| Ascorbic acid | 200 μl | 50 μg/ml |
| β-glycerophosphate | 2 ml | 10 mM |

Example 2

Cell Phenotype

The MSC cell population obtained as explained in Example 1 ("Isolation and culture of bone marrow MSC") without cell sorting or growth factor stimulation expressed high levels of mesenchymal markers (CD90, CD105 and CD73), consistent with their mesenchymal origin. Haematopoietic CD34 surface molecule was expressed at low levels (usually between 5% to 15% of the whole population). ALP marker representing the bone potential of the cells was also highly expressed (Table 1 and 2). A third of the CD34+ cells were also CD90+(FIG. 1—a low and high level of expression of CD90/CD34+).

TABLE 1

Phenotypic markers of MSC (percentage of cells deemed positive by FACS)

| | Whole cell population | | |
|---|---|---|---|
| | CD90* | CD34 | ALP |
| #1 | 95% | 4.3% | 9% |
| #2 | 92% | 5.9% | 11% |
| #3 | 98% | 18.5% | 6% |
| #4 | 99% | 3.1% | 7.8% |
| #5 | 99% | 7.3% | 9% |
| #6 | 97% | 9.2% | 9.5% |
| #7 | 85% | 15.8% | 8.7% |

*similar results are obtained for CD105 and CD73

TABLE 2

Phenotypic markers of MSC (percentage of cells deemed positive by FACS)

| | Whole cell population | | |
|---|---|---|---|
| | N | Mean | SD |
| ALP | 11 | 7.9 | 16.6 |
| CD105 | 11 | 91.8 | 7.9 |
| CD90 | 12 | 95.7 | 4.0 |
| CD73 | 13 | 94.7 | 3.4 |
| CD34 | 11 | 7.2 | 20.6 |

The cells were mainly negative for osteocalcin <33%.

Example 3

CD34 Positive Cell Isolation

At the end of the first expansion step carried out as explained in Example 1 ("Isolation and culture of bone marrow MSC") before cell sorting, the MSC cells were harvested off the flasks. The method of positive selection by flow cytometry sorting to isolate the CD90/CD34+ population was used. Cells were first stained with a specific APC-coupled anti-CD34 antibody solution. Then the cell population was injected through a Becton-Dickinson fluorescence-activated cell sorter to isolate CD34 labelled cells from the population. The CD34+ cells were then collected in a phosphate buffer saline solution.

An aliquot of the cells was analysed to check the purity. Out of $1\times10^8$ initial cells, on average about $50\times10^6$ cells were sorted whom 15 to 90% were CD90/CD34+ osteoprogenitors, corresponding to an enrichment of a factor of 10 to 30. These cells were further cultured under same conditions.

Example 4

Expansion Method

Isolated CD34+ cells obtained as explained in Example 3 were expanded in a 1 week culture protocol. About 70-75% of the isolated fraction survived to the purification steps. Those cells were incubated in standard medium containing plasma supplemented with growth factors and cytokines. Alternatively non-sorted cells could also be cultured. Similar results were obtained with or without sorting.

Cells incubated with haematopoietic factors (such as CSF2, CSF3, M-CSF, GM-CSF, IFN, TNF, or cytokines such as IL2) alone or in combination were able to grow at the same yield as the cells grown in standard conditions. However the yield of the cells incubating with angiogenic factors (such as FLT1, PDGF, VEGF, vWF, angiopoietin2, FGF1, FGF3 and EPO) alone or in combination were on average 25% higher than the yield obtained in standard conditions. More interestingly, the combination of both haematopoietic and angiogenic factors was able to give the highest increase in expansion yield, close to 50%, suggesting a synergistic effect of the combination.

Cells incubated in osteogenic medium were used as control and give a moderate expansion rate of the initial CD90/CD34+ initial population.

As an example, cells incubated with the haematopoietic factor GM-CSF in the presence of FGF-2 considerably increased the yield over that of GM-CSF or FGF-2 alone (Table 3).

TABLE 3

Yield of the expansion of CD90/CD34+ cells (% of the standard conditions)

|  | Standard | Haematopoietic GM-CSF | FGF-2 | Combination GM-CSF & FGF-2 |
|---|---|---|---|---|
| Culture 1 | 100% | 97% | 127% | 145% |
| Culture 2 | 100% | 112% | 142% | 162% |
| Culture 3 | 100% | 102% | 124% | 138% |
| Culture 4 | 100% | 89% | 103% | 148% |
| Culture 5 | 100% | 98% | 110% | 123% |
| Culture 6 | 100% | 105% | 130% | 145% |
| Mean | 100% | 98.2% | 148% | 178% |

Figure 2:
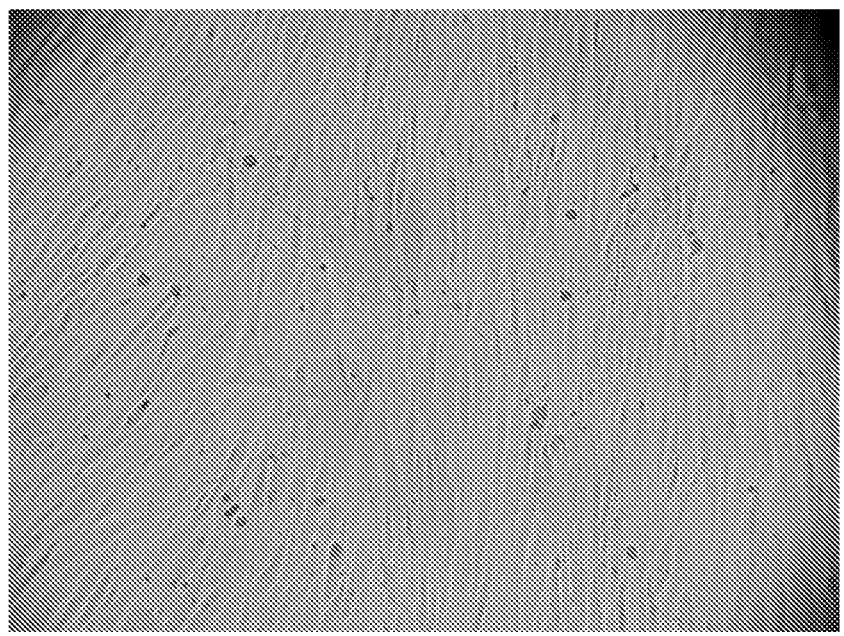
FIG. 2 illustrates light microscopic examination of the CD90/CD34+ cells after 1 week of culture.

Moreover, the morphology of the CD90/CD34+ cells after 1 week of culture was the same spindle-shape as initial bone forming cells (FIG. 2).

Those osteoprogenitor cells remained adherent at all times (of the culture period) suggesting that this new population would not be circulating and therefore distinct from circulating osteoblast lineages (such as ones of Eghbali-Fatourechi et al. 2007. Bone 40: 1370-7).

Figure 3:
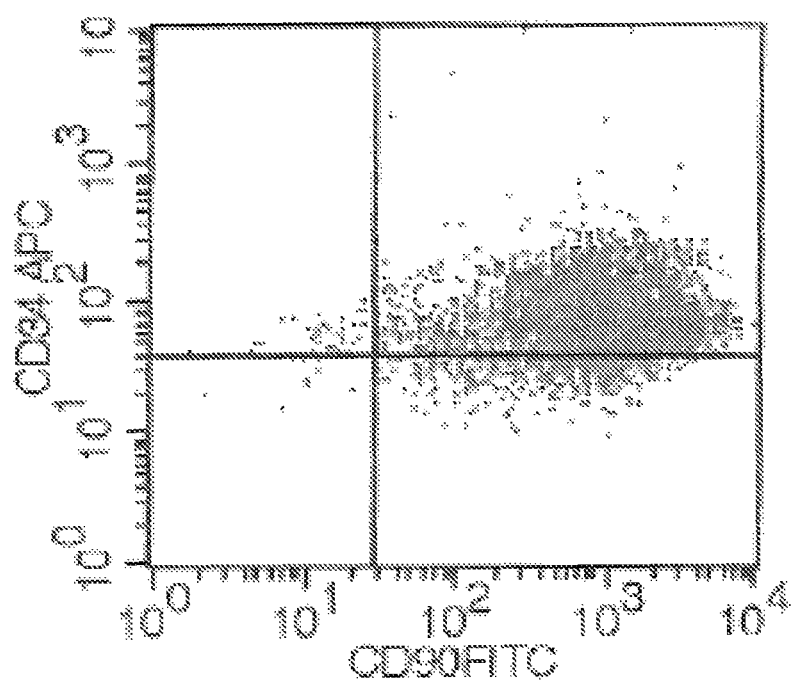
FIG. 3 illustrates dual-colour flow cytometric analysis of CD90 (FITC) and CD34 (APC) expression after expansion under supplemented culture conditions. The dot plot histogram represents 5000 events collected as list mode data.

Surface marker profile of these cells at the end of the expansion were analyzed in the standard condition of culture: CD34 maker was maintained at a high level while the other mesenchymal or bone specific markers remained unchanged supporting the finding of a new population sharing both osteogenic (ALP) and haematopoietic signature (CD34 positive) (Table 4 and FIG. 3).

TABLE 4

Phenotypic markers of CD90/CD34+ cells after 1 week of expansion in supplemented culture conditions (% of cells deemed positive by FACS)

| | CD34+ cell population | | |
|---|---|---|---|
| | N | Mean | SD |
| ALP | 11 | 69.2 | 15.3 |
| CD105 | 11 | 92.8 | 4.7 |
| CD90 | 12 | 92.9 | 1.9 |
| CD73 | 13 | 93.1 | 4.2 |
| CD34 | 11 | 51.6 | 19.0 |

Example 5

Bone Reconstructive Properties

Figure 4:
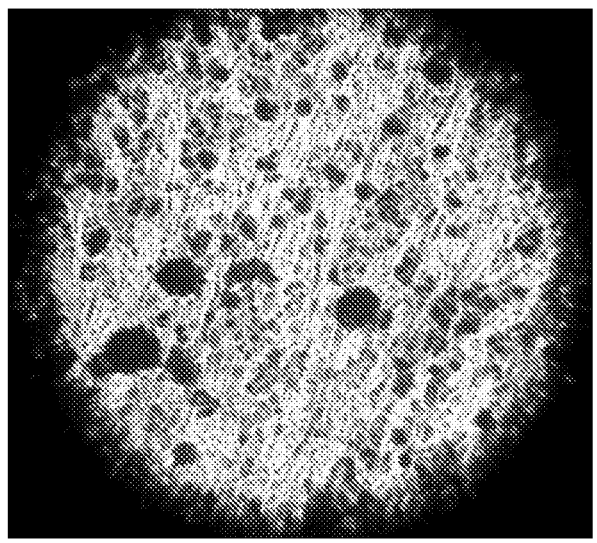
FIG. 4 illustrates mineralization (A) and ALP staining (B) by CD90/CD34+ cells
Figure 4:

Biological properties of this new population (as obtained in example 3, in the presence of a combination of GM-CSF and FGF-2) were assessed by measuring the ALP production (ALP staining) and their capabilities to form and mineralize new bone matrix. CD34+ cells produced a substantial amount of bone matrix (score of 2 out a maximum of 2) and were significantly positive to ALP staining process (score of 2 out a maximum of 2) suggesting that this population of cells was capable of a high bone reconstructive potential (FIG. 4). For comparison, standard MSC cultures give a bone matrix score of 1 to 1.5 and an ALP staining score of 1.5.

Figure 5:
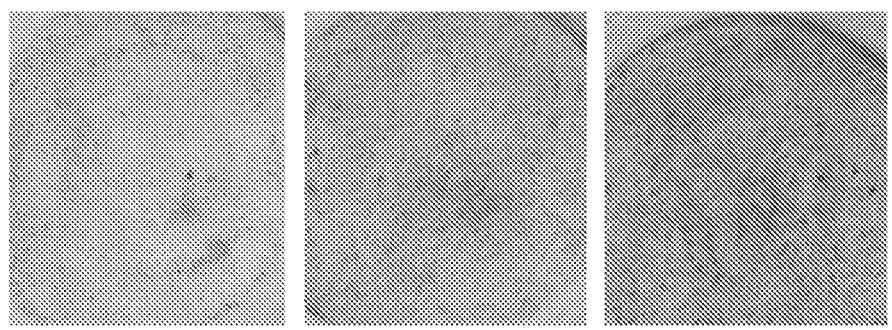
FIG. 5 illustrates dependence of mineralization ability on CD34+ percentage.

Interestingly, it was shown that the higher the % of CD34+ cells in the population the higher the mineralization capacity (FIG. 5).

Example 6

Expansion, Enrichment and Properties of MSC and Bone-Forming Cells

Proliferation in the Presence of Haematopoietic and/or Angiogenic Growth Factors (Table 5)

The cells were subjected to the enrichment protocol as explained in Example 1 ("Enrichment by culture").

As displayed in Table 5 (n=3), FGF-2 (2 ng/ml) induced the proliferation and expansion of a specific population of bone-forming cells as compared to the control condition (FBS 15%). Our data further revealed that in the presence of FGF-2 generation and/or expansion of this bone-forming cell population can be obtained and/or maintained using either GM-CSF (10 ng/ml) or IFN-gamma (10 ng/ml), and was significantly increased using FGF-1 (2 ng/ml), FGF-3 (2 ng/ml) or PDGF (1 ng/ml) angiogenic growth factors.

TABLE 5

Proliferation in the presence of haematopoietic and/or angiogenic growth factors

| Conditions | Factor* | Culture Yield % | % of increased proliferation rate versus FBS 15% | % of increased proliferation rate vs. FGF-2 alone |
|---|---|---|---|---|
| FBS 15% | — | 284 +/− 257 | 100 | — |
| FGF-2 | A | 537 +/− 69 | 189 | 100 |
| FGF-1[1] | A | 746 +/− 112 | 263 | 139 |
| FGF-3[1] | A | 605 +/− 50 | 213 | 113 |
| PDGF[1] | A | 756 +/− 110 | 266 | 141 |
| GM-CSF[1] | H | 524 +/− 61 | 185 | 98 |
| IFN-g[1] | H | 508 +/− 16 | 179 | 95 |

[1]In the presence of FGF-2;
*A = angiogenic and H = hematopoietic

Phenotypic Characterization (Table 6)

Flow cytometric analysis of the expanded bone-forming cells (n=3) demonstrated that this selected cell population exhibited a specific phenotypic profile, expressing CD34 together with typical mesenchymal cell markers such as CD105, CD73, and CD90, while lacking haematopoietic and endothelial cell surface markers such as CD45, CD133, and CD31 antigens.

TABLE 6

| | Phenotypic profile | | | | | | |
|---|---|---|---|---|---|---|---|
| | Haematopoietic cell marker | Mesenchymal cell markers | | | Endothelial cell markers | | |
| | CD45 % positive cells | CD105 % positive cells | CD73 % positive cells | CD90 % positive cells | CD133 % positive cells | CD31 % positive cells | CD34 % positive cells |
| FBS 15% | 3 +/− 1 | 66 +/− 2 | 74 +/− 19 | 90 +/− 8 | 15.7 +/− 13 | 2.2 +/− 0.7 | 9.0 +/− 11.8 |
| FGF-2 | 3 +/− 1.5 | 92 +/− 2 | 99 +/− 1 | 99 +/− 1 | 4.5 +/− 0.9 | 4.3 +/− 1.2 | 49 +/− 15 |

TABLE 6-continued

Phenotypic profile

| | Haematopoietic cell marker | Mesenchymal cell markers | | | Endothelial cell markers | | |
|---|---|---|---|---|---|---|---|
| | CD45 % positive cells | CD105 % positive cells | CD73 % positive cells | CD90 % positive cells | CD133 % positive cells | CD31 % positive cells | CD34 % positive cells |
| FGF-1[1] | 2.6 +/− 0.5 | 94 +/− 3 | 97 +/− 3 | 98 +/− 1 | 2.9 +/− 1.1 | 3.3 +/− 0.7 | 39 +/− 10 |
| FGF-3[1] | 2.2 +/− 0.8 | 93 +/− 2 | 99 +/− 1 | 98 +/− 1 | 5.7 +/− 3.3 | 3.4 +/− 0.9 | 42 +/− 8 |
| PDGF[1] | 2.2 +/− 0.4 | 93 +/− 2 | 99 +/− 1 | 97 +/− 1 | 4.9 +/− 2.2 | 3.3 +/− 0.7 | 34 +/− 8 |
| GM-CSF[1] | 1.4 +/− 1.3 | 93 +/− 3 | 99 +/− 1 | 98 +/− 1 | 3.3 +/− 0.6 | 3.6 +/− 0.5 | 40 +/− 7 |
| IFN-g[1] | 2.3 +/− 0.1 | 92 +/− 3 | 99 +/− 1 | 86 +/− 2 | 4 +/− 1.5 | 3.3 +/− 0.7 | 28 +/− 7 |

[1]In the presence of FGF-2

Figure 6:
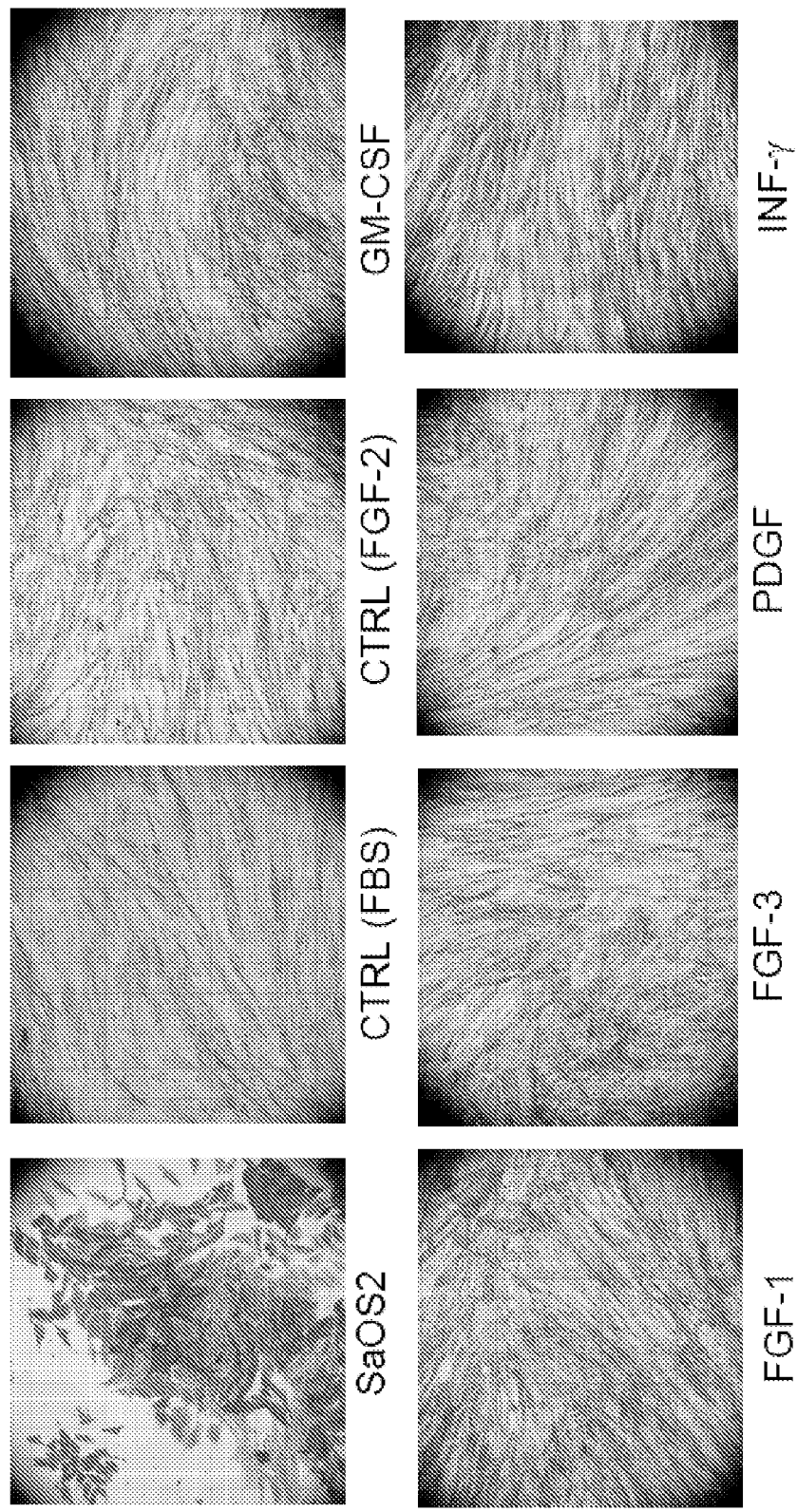
FIG. 6 illustrates osteogenic properties of cells by ALP staining.

Osteogenic Properties (Table 7, FIG. 6)

Flow cytometric analysis and ALP staining of the expanded bone-forming cell population indicated that these cells displayed strong osteogenic properties (n=3). Furthermore, it is interesting to note that IFN-gamma was shown to selectively and considerably increase both ALP expression and staining, thereby enhancing the osteogenic character of the cells.

TABLE 7

Osteogenic properties-ALP measurements

| | Osteogenic properties | | | |
|---|---|---|---|---|
| Conditions | ALP Expression (Flow Cytometry) % positive cells | ALP Enzymatic activity MFI | ALP Staining mU/mg protein | Semi-quantitative evaluation |
| FBS 15% | 21 +/− 11.1 | 2.6 | 10 | + |
| FGF-2 | 67 +/− 1 | 17.6 | 56 | ++ |
| FGF-1[1] | 66 +/− 2 | 15.6 | 69 | ++ |
| FGF-3[1] | 66 +/− 5 | 15.1 | 39 | ++ |
| PDGF[1] | 64 +/− 3 | 12.6 | 36 | ++ |
| GM-CSF[1] | 64 +/− 3 | 15.3 | 57 | ++ |
| IFN-g[1] | 82 +/− 2 | 28.7 | 318 | +++ |

[1]In the presence of FGF-2

Figure 7:
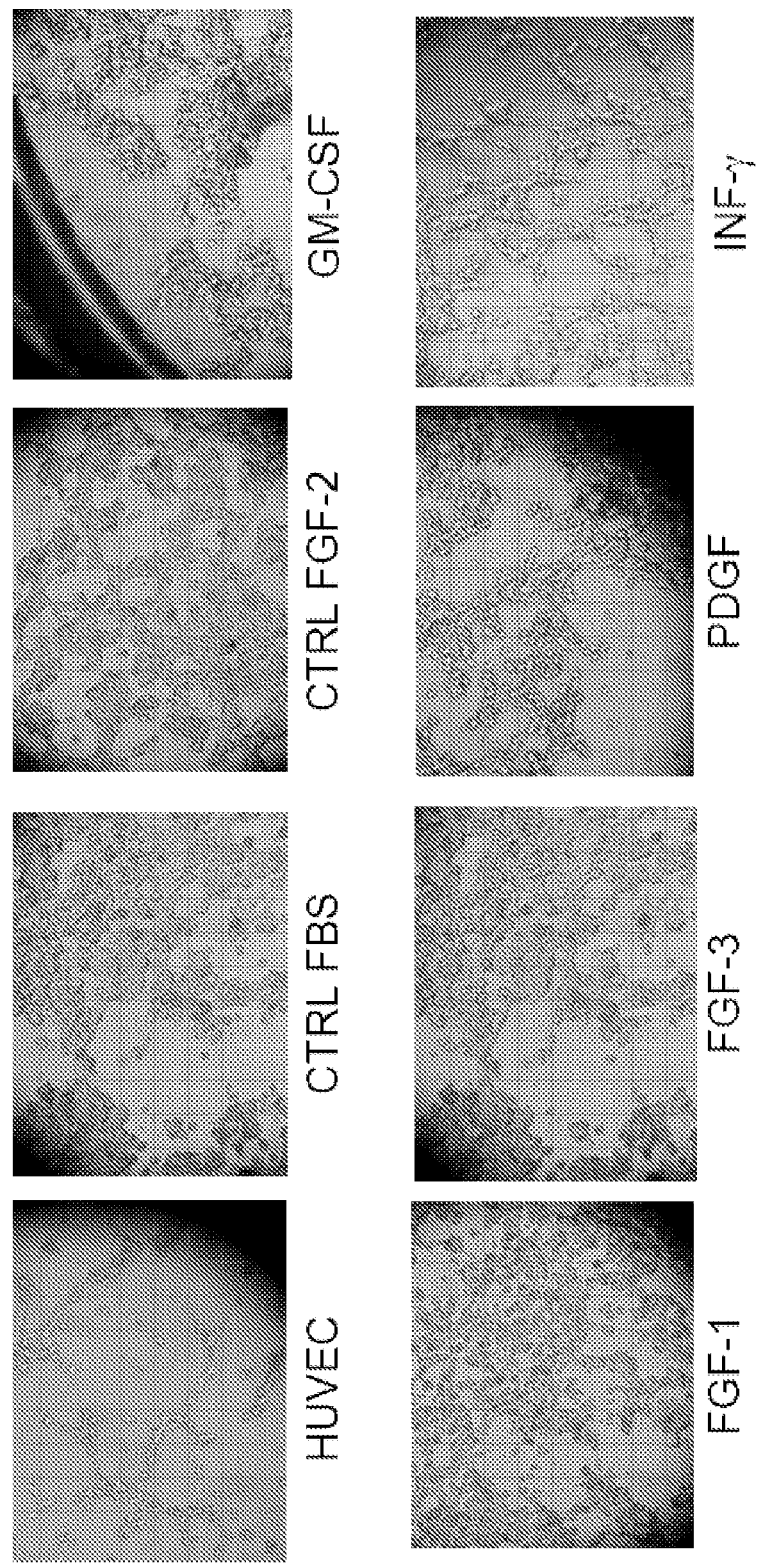
FIG. 7 illustrates pro-angiogenic properties of cells by capillary-like structure formation assay.

Pro-Angiogenic Properties and Capillary-Like Structure Formation Potential (Table 7, FIG. 7)

Flow cytometric analysis of the expanded bone-forming cells demonstrated upregulation of vWF and VEGF molecule expression (n=3). Moreover, as illustrated in FIG. 7 (n=1), our data indicated that this population of bone-forming cells was able to differentiate and organize into branched neo-vascular structures and pseudotubes in a Matrigel model. In addition, IFN-gamma was shown to clearly enhance this network formation as compared to controls (and other haematopoietic and/or angiogenic factors). These in vitro results show that both IFN-gamma and the expanded bone-forming cell population have the capacity to promote tube formation and the development of capillary-like structures (pro-angiogenic effect).

The invention claimed is:

1. A method for in vitro expanding of Mesenchymal Stem Cells (MSCs), comprising exposing said MSCs to fibroblast growth factor 2 (FGF-2); at least one of plasma or serum; and one or more factors selected from granulocyte monocytes CSF (GM-CSF), Interferon-γ (IFN-γ), platelet-derived growth factor (PDGF) and FGF-3.

2. The method according to claim 1 comprising exposing said MSCs to FGF-2; at least one of plasma or serum; and one or more factors selected from GM-CSF, PDGF, and FGF-3.

3. The method according to claim 1 comprising exposing said MSCs to FGF-2; at least one of plasma or serum; and IFN-γ.

4. A method for in vitro expanding of bone-forming cells, the method comprising exposing said bone-forming cells to FGF-2; at least one of plasma or serum: and one or more factors selected from GM-CSF, IFN-γ, FGF-1 and FGF-3, wherein said bone-forming cells are osteoblasts or osteoblastic cells.

5. The method according to claim 4 comprising exposing said bone forming cells to FGF-2; at least one of plasma or serum; and one or more factors selected from GM-CSF, FGF-1, and FGF-3.

6. The method according to claim 4 comprising exposing said bone forming cells to FGF-2; at least one of plasma or serum; and IFN-γ.

7. The method according to claim 4, wherein said bone-forming cells are osteoblasts.

8. The method according to claim 4, wherein the bone-forming cells express surface markers comprising CD105 and CD34 or surface markers comprising CD105, CD90, CD73, and CD34.

* * * * *